United States Patent [19]
Arntz et al.

[11] Patent Number: 5,100,852
[45] Date of Patent: Mar. 31, 1992

[54] COMPOUNDS OF CATALYSTS FOR DEALKOXYLATION OF GEM-DIALKOXY

[75] Inventors: Dietrich Arntz, Oberursel; Michael Baacke, Hanau; Peter Kleinschmit, Hanau; Guenter Prescher, Hanau, all of Fed. Rep. of Germany

[73] Assignee: Degussa Aktiengesellschaft, Frankfurt am Main, Fed. Rep. of Germany

[21] Appl. No.: 163,147

[22] Filed: Feb. 25, 1988

Related U.S. Application Data

[63] Continuation of Ser. No. 909,983, Sep. 22, 1986, abandoned.

[30] Foreign Application Priority Data

Oct. 2, 1985 [DE] Fed. Rep. of Germany ....... 3535128

[51] Int. Cl.$^5$ .............................................. B01J 29/18
[52] U.S. Cl. ...................................... 502/77; 502/78; 568/626; 568/691
[58] Field of Search .................. 568/626, 691; 502/77, 502/78; 423/328, 329

[56] References Cited

U.S. PATENT DOCUMENTS

| | | | |
|---|---|---|---|
| 1,902,169 | 3/1933 | Herrmann et al. | 568/691 |
| 3,013,985 | 12/1961 | Breck et al. | 502/78 |
| 3,322,690 | 5/1967 | Bilisoly | 502/78 |
| 3,328,439 | 6/1967 | Hamilton | 560/234 |
| 3,615,188 | 10/1967 | Kouwenhoven | 502/78 |
| 3,702,886 | 11/1972 | Argauer | 423/328 |

Primary Examiner—Vivian Garner
Attorney, Agent, or Firm—Beveridge, DeGrandi & Weilacher

[57] ABSTRACT

Catalytic dealkoxylation of gem-dialkoxy compounds for synthesizing vinyl ethers is disclosed. Zeolites of the mordenite or ZSM5 type with an $Na_2O/Al_2O_3$ molar ratio of 1:1.05 ($\pm 0.25$) are used as catalysts.

4 Claims, No Drawings

COMPOUNDS OF CATALYSTS FOR DEALKOXYLATION OF GEM-DIALKOXY

This application is a continuation of application Ser. No. 909,983, filed on Sept. 22, 1986, now abandoned.

The invention relates to the catalytic dealkoxylation of gem-dialkoxy compounds for synthesizing vinyl ethers, suitable catalysts and synthesis thereof.

The catalytic conversion of acetals to unsaturated ethers has long been known. According to Reppe et al., Ann. 601, 81–84 (1956) (according to C.A. 51:9578 b-f) a silver/asbestos catalyst, for example, is used. Also, according to German DE-OS 1957680 (C.A. 75:76155 y), noble metal containing catalysts are used for this purpose. While these catalysts exhibit satisfactory selectivity, the conversions, however, are low even if acetals of a simple structure are used. A further disadvantage is the high price of these catalysts.

U.S. Pat. No. 3,285,967 relates to the catalytic dealkoxylation on trilithium-orthophosphate containing catalysts. However, no details regarding the stabilities thereof are given.

A study of the suitability of several other different catalysts for synthesizing vinyl ethers has been published by I. A. Bogod et al. (Khim. Prom. 1972, 48(9), 657–60, translated in Soviet Chem. Ind. No. 9, 1972, 547–549).

This publication not only contains data on the selectivity and yields, but is the only publication in which catalyst/stability data, which are of great practical importance, were determined during the investigation.

According to this publication, the most stable catalyst was a potassium exchanged type A zeolite, which even after 1000 hours still had a selectivity of 99%, albeit with a conversion of only 60%.

The object of the present invention is a process for synthesizing vinyl ethers from acetals in the presence of a catalyst which ensures high stability and at the same time high conversion and high selectivity.

The object of the invention is the catalytic dealkoxylation of gem-alkoxy compounds of formula (I):

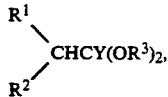

in which $R^1$ and $R^2$ represent $C_1$–$C_3$ alkyl, aryl or H, and especially methyl, $R_3$ represents methyl or ethyl, Y represents H or methyl at elevated temperature in the gas phase on an Na-exchanged zeolite as the catalyst, wherein zeolites are used of the mordenite or ZSM5 type with an $Na_2O/Al_2O_3$ molar ratio of 1:1.05 ($\pm 0.25$), preferably 1:1.05 ($\pm 0.15$), especially 1:1.05 ($\pm 0.05$).

Vinyl methyl and vinyl ethyl ethers and the substituted vinyl methyl and vinyl ethers corresponding to the starting compounds are obtained as products.

The reaction proceeds according to the following equation:

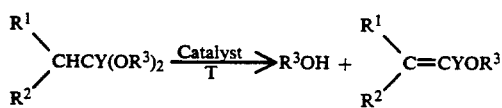

in which $R^1$, $R^2$, $R^3$ and Y have the meanings indicated above.

The dimethyl and diethyl acetals of acetaldehyde, propionaldehyde, butyraldehyde and isobutyraldehyde, and dimethyl ketal are preferably used. However, the conversion is also possible with phenylacetaldehyde dimethyl acetal.

The reaction takes place at temperatures between 200° and 450° C., preferably 260° and 360° C., especially between 280° and 340° C. The reaction pressure is low enough for the acetals or ketals not to condense on the catalyst under the reaction conditions, and is generally between 0 and 2 gauge atmospheres, although preferably the operation is performed without superatmospheric pressure.

As catalysts, zeolites are used of the mordenite or ZSM5 type with an $Na_2O/Al_2O_3$ molar ratio of 1:1.05 ($\pm 0.25$), preferably 1:1.05 ($\pm 0.15$), especially 1:1.05 ($\pm 0.05$).

Classification of the zeolites employed in accordance with the invention is according to Breck "Zeolite Molecular Sieves", John Wiley & Sons, 1974, p. 373 and p. 231, on the basis of the X-ray diffraction patterns. Zeolites, in general, are described in Kirk-Othmer, Encyclopedia of Chemical Technology, 3rd Edition, Vol. 15, pp. 638–669.

The examples which follow contains two prior art processes (German DE-OS 321 2 106 and DE-OS 281 7 576) by means of which zeolites of the ZSM5 and mordenite type can be synthesized. However, they can also be synthesized in other ways as is known in the art.

The zeolites obtained thereby are converted by known processes to the H-form and are then treated in such a way with sodium hydroxide solution that an $Na_2O/Al_2O_3$ molar ratio of 1:1.05 ($\pm 0.25$), preferably 1:1.05 ($\pm 0.15$), especially 1:1.05 ($\pm 0.05$) results in the end product.

For this purpose, a 5 to 40 weight percent suspension, relative to the total weight of the suspension, of the zeolite converted to H-form is prepared in aqueous sodium hydroxide solution, stirred for 0.1 to 20 hr at 20° to 100° C., preferably 0.5 to 5 hr at 50° to 80° C., and then evaporated to dryness. In this process, the sodium hydroxide concentration is adjusted such that the desired Na/Al molar ratio in the end product is achieved (impregnation). The reaction time decreases with increasing temperature, and preferably the zeolite is converted at 70° C. to 80° C. within 2 to 3 hr.

Another way of synthesizing the catalyst used according to the invention resides in preparing a 5 to 40 weight percent suspension in water of a mordenite or ZSM5 zeolite converted to the H-form and then, with monitoring of the pH of the suspension, adding an aqueous 2 to 50 weight percent, preferably 5 to 10 weight percent, sodium hydroxide solution with stirring at 20° to 100° C., preferably 50° to 80° C., within 0.1 to 10 hr, preferably 0.5 to 5 hr (ion exchange). Addition of sodium hydroxide solution is continued as long as the pH does not change, and this process is terminated only when the pH rises suddenly. It goes without saying that if suitable apparatus is available, the operation can also be performed under pressure and at higher temperatures.

After the suspension is cooled, the solid is filtered off and dried at 80° to 200° C., preferably 140° C. The water content then amounts to 3 to 20 weight percent. Although the catalysts obtained in powder form in these ways and subsequently heat-treated at 250° to 900°

C. (1 to 20 hr), preferably 1 to 5 hr at 600° to 800° C., have in principle the desired properties for conversion of acetals and ketals, it is demonstrated by experience that the use of cylindrical or spherical pellets having the normal dimensions is advisable, for example, in a fixed-bed reactor, whereas a finely divided catalyst powder is usable in a fluidized-bed reactor.

When fabricating these pellets, it is advantageous to use molding auxiliaries such as, for example, silica sol in a proportion of 1 to 5 ml of silica sol (40 weight percent $SiO_2$) per 5 g of zeolite, which preferably is available in the non-heat-treated condition (approximately 10 weight percent $H_2O$). The proportion of the molding agent can be varied within wide limits. Silica sol of this type is well known in the art. Needless to say that it is necessary to take into consideration the lower limit at which the strength of the molded product still withstands the mechanical strains in the reactor, as well as an upper limit at which the catalytically active material is so highly diluted that the conversion declines perceptibly. Following molding by a known process, the pellets are dried at 100° to 150° C. and then heat-treated, preferably for 0.5 to 20 hr at 300° to 800° C.

Reactivation of a spent catalyst to the original selectivity can be achieved simply by passing air through the reactor at a temperature of 400° to 600° C., preferably 450° to 530° C.

It has been found that it is also possible, without yield losses, to use acetal containing mixtures which are obtained by simple distillation even without the extraction from the reaction solution described in German DE-OS 3403426 and which, in the case of dimethyl acetal, for example, contain 25 to 30 weight percent of methanol and 2 to 5 weight percent of acetaldehyde; mixtures which in many cases lead to considerable formation of dimethyl ether as an undesired by-product.

Before the acetal or ketal is introduced into the reactor, it can be preheated to the reaction temperature. However, it is also possible to supply the necessary heat to the catalyst by preheating.

Preferably, the catalyst is loaded with 0.05 to 3 kg, desirably 0.3 to 1.5 kg, of acetal per kg of catalyst per hour.

The reaction gases flowing out of the reactor are then rectified directly in a column located downstream. Unreacted acetals and ketals and alcohol formed during the reaction as well as alcohol present from the start remain in the bottoms.

With the process of the invention, high stability and, at the same time, constantly high selectivity and high conversion are achieved, provided the Na-exchanged mordenites and ZSM5 zeolites are used. In contrast, in the prior art (Bogod et al.), specifically in the use of an Na-exchanged Y-type zeolite is used, only a very low stability and very low selectivity were recorded.

The following examples are illustrative of the present invention.

EXAMPLE 1

Synthesizing the mordenite type zeolite a) A solution of 2.07 kg of NaOH and 4.26 kg of sodium aluminate (34.35% $Na_2O$, 46.54% $Al_2O_3$) in 20 liters of $H_2O$ is added to a suspension of 33.1 kg of precipitated silicic acid (89% $SiO_2$) in 220 liters of $H_2O$. The mixture is stirred in a 300 liter autoclave for 77 hr at 180° C. and the crystalline product filtered off and washed with 300 liters of water. According to the X-ray diffraction pattern, the product is a nicely crystalline zeolite of the mordenite type.

Analysis
5.29% $Na_2O$
9.57% $Al_2O_3$
73.56% $SiO_2$
10.25% weight loss (1000° C.)

b) For conversions to the H-form, 2 kg of Na mordenite from Example 1(a) is suspended in 20 liters of 2 N $H_2SO_4$, stirred for 2 hr at 80° C. and filtered off. The treatment is repeated twice.

Analysis
0.30% $Na_2O$
6.57% $Al_2O_3$
74.64% $SiO_2$
16.53% weight loss (1000° C.)

EXAMPLE 2

Synthesizing the ZSM5 type zeolite a) A solution of 0.56 kg of NaOH and 0.65 kg of sodium aluminate (39.35% $Na_2O$, 46.54% $Al_2O_3$) in 40 liters of $H_2O$ is added to a suspension of 25 kg of precipitated silicic acid (89% $SiO_2$) in a solution of 10.76 kg of 1,6-diaminohexane in 220 liters of $H_2O$. The mixture is stirred for 70 hr at 180° C., filtered off, washed with 300 liters of $H_2O$ and dried for 24 hr at 120° C. The product consists of well crystallized zeolite of the ZSM5 structure type.

Analysis:
0.56% $Na_2O$
1.65% $Al_2O_3$
94.26% $SiO_2$
1.80% weight loss (1000° C.)

b) For conversion to the H-form, 1 kg of ZSM5 according to Example 2 is stirred in 10 liters of 1 N $H_2SO_{SO4}$ for 2 hr at 80° C. and then filtered off. The treatment is repeated one more time.

Analysis:
0.02% $Na_2O$
1.60% $Al_2O_3$
93.65% $SiO_2$
2.05% weight loss (1000° C.)

It should be noted that any suitable precipitated silica may be used for purposes of the invention, such as those described in Ullmann's Encyclopedia of Chemical Technology, 4th Edition, Vol. 21, pp. 465–467, relied on and incorporated herein by reference. A typical precipitated silica used herein is Degussa Product VN3; see Ullmann's, id. p. 467.

EXAMPLE 3

The zeolites converted to the H-form are converted by impregnation (catalysts A to H) or by ion exchange (catalyst J) into the Na-form which is usable according to the invention.

Impregnation (catalysts A–H)

Zeolite existing in the H-form is suspended in an aqueous NaOH solution, stirred for 2 hr at 80° C. and then evaporated to dryness.

Ion exchange (catalyst J)

Zeolite existing in the H-form is suspended in water. As a result, a pH of approximately 4 is established. Within 2 hr at 80° C., 1 N sodium hydroxide solution is added until the pH rises sharply. After the suspension is cooled, the solid is filtered off and dried at 140° C.

Molding

The zeolite powders A–J obtained are processed with silica sol, LUDOX HS 40, (40% $SiO_2$) to a moldable composition (0.475 ml of silica sol per g of zeolite) and molded into cylindrical pellets (diameter 3 cm, length 2 to 4 mm) using an Alexanderwerke granulator, then dried for 16 hr at 125° C. and heat treated for 4 hr at 450° C.

Table 1 lists the $Na_2O/Al_2O_3$ ratios of catalysts A to J synthesized according to the instructions given above and the associated quantitative proportions of reagents.

TABLE 1

| Catalyst | g Zeolite | g NaOH | ml $H_2O$ | $Na_2O/Al_2O_3$ molar ratio in the end product |
|---|---|---|---|---|
| A | 500 g Mordenite | 3.0 | 1000 | 0.75 |
| B | 600 g Mordenite | 8.3 | 1000 | 0.95 |
| C | 600 g Mordenite | 10.7 | 1000 | 1.05 |
| D | 600 g Mordenite | 11.9 | 1000 | 1.10 |
| E | 3000 g Mordenite | 59.5 | 6000 | 1.27 |
| F | 500 g Mordenite | 20.4 | 1000 | 1.63 |
| G | 500 g ZSM5 | 5.65 | 1000 | 0.95 |
| H | 500 g ZSM5 | 6.20 | 1000 | 1.05 |
| J | 1200 g Mordenite | 86.35 | 2500 | 1.03 |

Table 1 are to be found in the following examples.

EXAMPLE 4

Conversion of acetaldehyde dimethyl acetal (DMA)

1640 g of catalyst J synthesized according to Example 3 was charged into a 3 meter long reactor with a diameter of 29 mm, maintained at a reaction temperature of 310° C. by an electrical heater, then 800 g of acetaldehyde dimethyl acetal (DMA) per hour was passed over the catalyst and the reaction gases were rectified (distilled) directly in a column located downstream After an operating period of 50 hours, vinyl methyl ether in a purity of 99.7% was obtained at a conversion of 93% at the column head with a selectivity of 99.5%. After an operating period of 1000 hours, the conversion and selectivity were still unchanged. In both cases, 6.9% of DMA, relative to the DMA feed, and 92.6% of methanol were recovered in the column bottoms.

EXAMPLE 5

Conversion of a mixture of DMA, methanol and acetaldehyde 960 g of catalyst J synthesized according to Example 3 was charged into a reactor of 2 m length and 29 mm diameter, maintained at a temperature of 300° C., then 690 g of mixture with a content of 24.5 weight percent of methanol, 2.1 weight percent of acetaldehyde and 73.4 weight percent of DMA was passed through the reactor per hour and the reaction gas was directly rectified by distillation in a column. At the column head, vinyl methyl ether was isolated with a selectivity of 99.1%, relative to the 90.6% of DMA which had reacted. In addition to vinyl methyl ether, the distillate contained 2.8 weight percent of acetaldehyde. Unreacted DMA and methanol which had been formed as well as methanol in the feed remained completely in the bottoms.

EXAMPLE 6

40 g of catalyst J synthesized according to Example 3 was charged into a reactor of 12 mm diameter, maintained at a temperature of 300° C. with a salt bath. At a feed rate of 60 ml of DMA per hour, a conversion of 88% with a selectivity of VME of 99% was obtained.

EXAMPLES 7 TO 15

Corresponding to Example 4, the following catalysts were used:

TABLE 2

| Example No. | $Na_2O/Al_2O_3$ catalyst | Reaction Temperature (°C.) | Conversion (%) | Selectivity to VME (%) |
|---|---|---|---|---|
| 7 | E 1.27 | 340 | 85 | 92.5 |
| 8 | D 1.10 | 340 | 91 | 98.3 |
| 9 | C 1.05 | 300 | 82 | 96.8 |
| 10 | H 1.05 | 300 | 89 | 95.4 |
| 11 | B 0.95 | 280 | 87 | 96.2 |
| 12 | A 0.75 | 280 | 93 | 91.3 |
| 13 | G 0.95 | 300 | 93 | 92.4 |
| 14 | F 1.63 | 300 | 50 | 94.3 |
| 15 | J 1.03 | 300 | 88 | 99.0 |

EXAMPLES 7–15

Corresponding to Example 5, acetals other than DMA were converted to vinyl ethers. Catalyst C according to Example 3 was used.

Table 3 shows the results obtained:

TABLE 3

Reactor-wall temparture: 300° C.
Catalyst load: 1.5 kg acetal (ketal)/kg catalyst/hr

| Acetal (Ketal) | Ether | Conversion (%) | Selectivity to ether (%) |
|---|---|---|---|
| 16) $CH_3-CH_2-CH\begin{matrix}OCH_3\\OCH_3\end{matrix}$ | $CH_3-CH=CH-OCH_3$ | 97 | 98.0 |
| 17) $CH_3-CH\begin{matrix}OEt\\OEt\end{matrix}$ | $CH_2=CH-OEt$ | 98 | 80 |

TABLE 3-continued

Reactor-wall temparture: 300° C.
Catalyst load: 1.5 kg acetal (ketal)/kg catalyst/hr

| Acetal (Ketal) | Ether | Conversion (%) | Selectivity to ether (%) |
|---|---|---|---|
| 18) $(CH_3)_2CH-CH(OCH_3)_2$ | $(CH_3)_2C=CH-OCH_3$ | 93 | 77 |
| 19) $(CH_3)_2C(OCH_3)_2$ | $CH_2=C(CH_3)-OCH_3$ | 93 | 90 |
| 20) $C_6H_5-CH_2-CH(OCH_3)_2$ | $C_6H_5-CH=CH-OCH_3$ | 40 | 25 |

We claim:

1. A process for synthesizing a catalyst comprising providing an H-exchanged zeolite of the mordenite or ZSM5 type, suspending said zeolite in an aqueous sodium hydroxide solution, sitrring said zeolite in said solution for a sufficient time to react the zeolite with the solution and for subsantial completion of the reaction, evaporating to dryness, to thereby recover a solid product, with the provision that the Na/Al molar ratio in suspension amounts to 1:1.05 (±0.25).

2. The process for synthesizing a catalyst according to claim 1 wherein after the H-exchanged zeolite of the mordenite or ZSM5 type is suspended in water, the pH is monitored, and while monitoring the pH, adding thereto an aqueous sodium hydroxide solution with stirring until the pH rises suddenly and, thereafter cooling the solution, after the solution is cooled, then filtering off the solid, drying the solid and heat treating the solid at elevated temperature.

3. The process for synthesizing a catalyst according to claim 2 wherein after recoverng the solid Na-exchanged zeolite, which is in powder form, mixing therewith silica sol in a sufficient proportion until a pasty moldable composition is formed, thereafter molding said composition into pellets, drying and heat treating the molded products.

4. The process of claim 3 wherein the silica sol contains 50 to 90 weight percent $H_2O$.

* * * * *